(12) United States Patent
Motomura et al.

(10) Patent No.: US 7,502,440 B2
(45) Date of Patent: Mar. 10, 2009

(54) RADIODIAGNOSTIC APPARATUS

(75) Inventors: Nobutoku Motomura, Nasushiobara (JP); Akiyosi Kinda, Otawara (JP)

(73) Assignees: Kabushiki Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 145 days.

(21) Appl. No.: 11/396,450

(22) Filed: Apr. 4, 2006

(65) Prior Publication Data

US 2006/0222145 A1 Oct. 5, 2006

(30) Foreign Application Priority Data

Apr. 5, 2005 (JP) ............... 2005-109088

(51) Int. Cl.
*A61B 6/03* (2006.01)
(52) U.S. Cl. ............... 378/19; 378/4; 378/901
(58) Field of Classification Search .............. 378/4, 378/19, 63, 901; 250/363.07
See application file for complete search history.

(56) References Cited

U.S. PATENT DOCUMENTS 4,550,371 A * 10/1985 Glover et al. ............ 378/4
6,339,223 B1 * 1/2002 Motomura et al. ...... 250/363.07
6,856,666 B2 * 2/2005 Lonn et al. .............. 378/8

FOREIGN PATENT DOCUMENTS

JP 2000-28728 1/2000

OTHER PUBLICATIONS

Sourbelle et al., Reconstruction from truncated projections in CT using adaptive detruncation, Published online Feb. 9, 2005, European Radiology, vol. 15, No. 5, pp. 1008-1014.*
Starman et al., Estimating 0th and 1st Moments in C-Arm CT Data for Extrapolating Truncated Projections, Feb. 17, 2005, Medical Imaging 2005: Image Processing, vol. 5747, pp. 378-387.*
Takahashi et al., Truncation correction of fan beam transmission data for attenuation correction using parallel beam emission data on a 3-detector SPECT system, 2004, Nuclear Medicine Communications, vol. 25, No. 6, p. 623-630.*
2IV283, "A Method for Correcting a Truncation Which Appears in a CT Image in a PET-CT Apparatus",The 44th Annual Meeting of Japanese Society of Nuclear Medicine, Nov. 4-6, 2004, p. 64.

* cited by examiner

*Primary Examiner*—Chih-Cheng G Kao
*Assistant Examiner*—John M Corbett
(74) *Attorney, Agent, or Firm*—Oblon, Spivak, McClelland, Maier & Neustadt, P.C.

(57) ABSTRACT

A radiodiagnostic apparatus includes a data collection unit, a primary correction unit, a body contour detection unit, a secondary correction unit, and a reconstruction unit. The primary correction unit calculates a plurality of primary extrapolation expression candidates for correcting second projection data so as to obtain third projection data candidates formed from the second projection data and a plurality of primary extrapolation expression candidates and for obtaining third projection data from the plurality of third projection data candidates.

14 Claims, 6 Drawing Sheets

RADIODIAGNOSTIC APPARATUS

BACKGROUND OF THE INVENTION

1. Field of the Invention

The present invention relates to a radiodiagnostic apparatus for detecting a body contour of an object from a CT image obtained by a transmission CT apparatus.

2. Description of the Related Art

A transmission computerized tomography (TCT) apparatus in radiodiagnostic apparatuses is to obtain a tomographic distribution of radiographic transmission of an object by rotating a radiation source of radiation (X-ray or gamma ray) installed outside the object and a detector as a pair around an axis of the object and measuring the radiation having transmitted from the object. As a typical transmission CT apparatus, an X-ray CT apparatus, or a transmission CT mechanism combined with a single photon emission computed tomography (SPECT) apparatus or a positron emission tomography (PET) apparatus, which is a nuclear medicine apparatus, can be given as examples.

A PET apparatus, for example, detects gamma rays (photons) emitted from a Radioisotope (RI) dosed to an object and measures a distribution of the RI in an inside of the object. The radiated gamma rays are attenuated in the subject. Therefore, in order to conduct quantitative measurement by the PET apparatus, it is necessary to measure an attenuation distribution in the inside of the object by a transmission CT mechanism using an external gamma radiation source and to make correction according to a measured amount.

Among transmission CT apparatuses using the external gamma radiation source, a transmission CT apparatus using a fan beam collimator has less scattered radiation since gamma rays are collimated at two points, at the radiation source and at the collimator, and has an advantage that an attenuation coefficient distribution in an inside of an object can be measured accurately. On the other hand, since an effective acquisition field of the detector, which is a range limited by the collimator, is narrowed when using the fan beam collimator, if the object larger than the effective acquisition field is measured, a region outside the effective acquisition field of the object can not be picked up. Thus, truncation (artifact) is generated due to incomplete reconstruction of an image. Also, an image can not be taken accurately due to truncation in the effective acquisition field.

Truncation can be suppressed by using a apparatus with a sufficiently large radiographic acquisition field, but that results in the apparatus unnecessarily enlarged and increases apparatus cost. Thus, a method for solving the truncation problem with the use of software without changing the hardware mechanism of the apparatus has been proposed.

Methods for solving the truncation problem include a method for approximating a body contour of an object as an oval in a SPECT image obtained from a SPECT apparatus, which is an emission CT apparatus, and a method in which a Snake function is applied to by the SPECT image (IEEE Trans. Nucl Sci., Vol. 47, No. 3, pp 989-993).

Also, as a method for solving the truncation problem, there is a method in which a body contour of an object is detected from the SPECT image and a total sum value of projection data and the center of gravity of the CT image are calculated by oval approximation using data representing the body contour, and then, a truncated portion is estimated from the total sum value of the projection data and the center of gravity of the CT image and a quadratic expression is extrapolated into the projection data.

However, according to the prior art, it is necessary to detect the body contour from outside the truncation CT apparatus, that is, an emission CT apparatus. Moreover, there is a problem of a low detection accuracy of the body contour in the method for estimating the body contour from the CT image data obtained by the emission CT apparatus.

SUMMARY OF THE INVENTION

The present invention has taken into consideration the above-described problems, and it is the first object of the present invention to provide a radiodiagnostic apparatus such that an attenuation distribution can be accurately measured, and a truncation correction can be made accurately with high accuracy.

Also, the present invention has taken into consideration the above-described problems, and it is the second object of the present invention to provide a radiodiagnostic apparatus such that a body contour with high accuracy can be detected only from a transmission CT apparatus.

To solve the above-described problems, the present invention provides a radiodiagnostic apparatus, comprising: a data collection unit for collecting a first projection data obtained at a projection angle within a projection angle range in which the whole portion of an object is within an effective acquisition field of a detector, and for collecting a second projection data obtained at a projection angle within a projection angle range in which a part of a truncated portion is out of the effective acquisition field of the detector, when the effective acquisition field of the detector is defined as a range limited by a collimator; a primary correction unit for calculating a plurality of primary extrapolation expression candidates for correcting said second projection data on the basis of a difference between a total sum value of said first projection data and a total sum value of said second projection data so as to obtain a plurality of third projection data candidates formed from said second projection data and said plurality of primary extrapolation expression candidates and for obtaining third projection data from said plurality of third projection data candidates on the basis of a difference between a center of gravity of the third projection data estimated from the center of gravity of said first projection data and a center of gravity of said plurality of third projection data candidates; a body contour detection unit for detecting position information of a body contour in said second projection data on the basis of said third projection data; a secondary correction unit for acquiring a secondary extrapolation expression for correcting said second projection data on the basis of said position information of the body contour and for obtaining fourth projection data formed from said second projection data and said secondary extrapolation expression; and a reconstruction unit for reconstructing an image on a slice-by-slice basis on the basis of said first projection data and said fourth projection data.

To solve the above-described problems, the present invention provides a radiodiagnostic apparatus, comprising: a data collection unit for collecting a first projection data obtained at a projection angle within a projection angle range in which the whole portion of an object is within an effective acquisition field of a detector, and for collecting a second projection data obtained at a projection angle within a projection angle range in which a part of a truncated portion is out of the effective acquisition field of the detector, when the effective acquisition field of the detector is defined as a range limited by a collimator; a primary correction unit for calculating a plurality of primary extrapolation expression candidates for correcting said second projection data on the basis of a difference between a total sum value of said first projection data and a total sum value of said second projection data so as to obtain a plurality of third projection data candidates formed from said second projection data and said plurality of primary extrapolation expression candidates and for obtaining third projection data from said plurality of third projection data candidates on the basis of a difference between a center of gravity of the third projection data estimated from said first projection data and a center of gravity of said plurality of third projection data candidates; a body contour detection unit for detecting position information of a body contour in said second projection data on the basis of said third projection data; a secondary correction unit for acquiring a secondary extrapolation expression for correcting said second projection data on the basis of said position information of the body contour and for obtaining fourth projection data formed from said second projection data and said secondary extrapolation expression; and an attenuation distribution correction unit for measuring an attenuation distribution on the basis of said fourth projection data and for correcting an image on the basis of said emission data by said attenuation distribution.

To solve the above-described problems, the present invention provides a radiodiagnostic apparatus, comprising: a data collection unit for collecting a first projection data obtained at a projection angle within a projection angle range in which the whole portion of an object is within an effective acquisition field of a detector, and for collecting a second projection data obtained at a projection angle within a projection angle range in which a part of a truncated portion is out of the effective acquisition field of the detector, when the effective acquisition field of the detector is defined as a range limited by a collimator; a additional processing unit for obtaining an addition value on the basis said first projection data: a estimated processing unit for estimating a position the center of gravity at a projection angle of said second projection data by said first projection data: a body contour estimated unit for estimating a position of the body contour in said second projection data on the basis said addition value and said position of the center of gravity: a projection data estimated unit for estimating a data that it is equivalent in the truncated portion in said second projection data.

The radiodiagnostic apparatus as described above make an attenuation distribution possible to be accurately measured, and a truncation correction possible to be made accurately with high accuracy.

Furthermore, the radiodiagnostic apparatus as described above make a body contour with high accuracy possible to be detected only from a transmission CT apparatus.

DESCRIPTION OF THE PREFERRED EMBODIMENTS

A preferred embodiment of a radiodiagnostic apparatus according to the present invention will be described with reference to the attached drawings.

Figure 1:
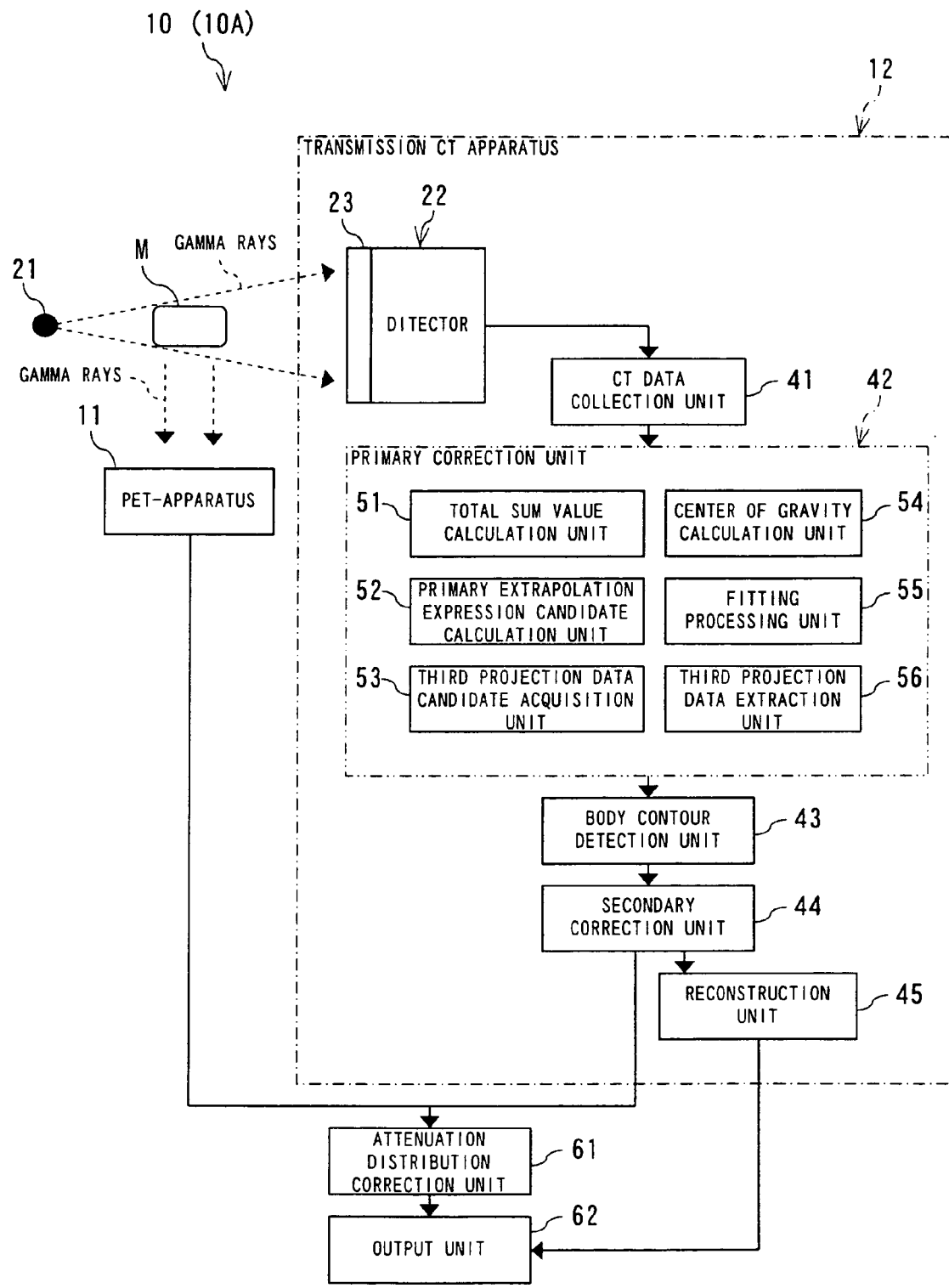
FIG. 1 is a schematic diagram of a preferred embodiment of a radiodiagnostic apparatus according to the present invention.

FIG. 1 shows a schematic diagram of a preferred embodiment of a radiodiagnostic apparatus according to the present invention.

FIG. 1 shows a radiodiagnostic apparatus 10 provided with at least one transmission CT apparatus having an external radiation source. In this preferred embodiment, a PET-CT apparatus 10A, which is a complex machine of a PET apparatus 11 as an emission CT apparatus not having an external radiation source and a transmission CT apparatus 12 having a gamma radiation source will be used as an example of the radiodiagnostic apparatus 10. It is to be noted that the emission CT apparatus is not limited to the PET apparatus but also a SPECT apparatus, for example, may be used. Also, as the transmission CT apparatus, a transmission CT apparatus having an X-ray source may be used.

The PET apparatus 11 of the PET-CT apparatus 10A collects PET data (emission data) by detecting gamma rays (photons) emitted from RI dosed to a object M.

On the other hand, the transmission CT apparatus 12 is provided with a gamma radiation source 21 for radiating gamma rays as radiation toward the object M and a detector 22 for outputting a signal representing a position at which the gamma rays having transmitted the object M fall on and an energy signal corresponding to energy of the incident radiation. A side which confronts the gamma radiation source 21 on the detector 22, a collimator 23 having a large number of openings of honeycomb shape, for example, arranged two-dimensionally in a direction the gamma radiation by means of a bulkhead composed by a radiation shielding material such as lead, and the detector 22 detects information on a radiation position of the radiation within the object M.

A detector of the PET apparatus 11 (not shown), the gamma radiation source 21 and the detector 22 are integrally supported on a frame, not shown, capable of rotation around anaxis of the object M. The detector of the PET apparatus 11 and the detector 22 are constituted so that the gamma radiation falls on individual projection angles while being rotated by an extremely small angle around an axis of the object M.

Moreover, in the transmission CT apparatus 12, a CT data collection unit 41, a primary correction unit 42, a body contour detection unit 43, a secondary correction unit 44 and a reconstruction unit 45 are provided.

The CT data collection unit 41 receives electric signals for 360 degrees at a plurality of projection angles (view angles) from the detector 22 while rotating the gamma radiation source 21 and the detector 22 around the object M and collects them as projection data (transmission projection data) for individual projection angles.

Here, the collimator 23 is roughly classified as one of a parallel collimator and a fan beam collimator according to the form of its opening. When the collimator 23 is a parallel collimator, the projection data collected at the CT data collection unit 41 is parallel beam data. On the other hand, when the opening of the collimator 23 is the fan beam collimator, the projection data collected at the CT data collection unit 41 is the fan beam data, and in this case, processing to convert the fan beam data to the parallel beam data is performed by a converting unit (not shown) provided within the CT data collection unit 41 or separately from the CT data collection unit 41.

Moreover, when the fan beam collimator is used as the collimator 23, the gamma radiation is to be collimated at the two points of the gamma radiation source 21 and the collimator 23. Thus, when the fan beam collimator is used, there is an advantage that it has less scattered radiation and the attenuation distribution within the object M can be measured accurately. On the other hand, a range limited by the collimator becomes an effective acquisition field of the detector 22, but when using the fan beam collimator, the effective acquisition field of the detector 22 is narrowed. Therefore, when a portion of the object M is to be measured, a part of the portion protrudes from the effective acquisition field and truncation is generated in a CT image due to incomplete reconstruction. Thus, when the fan beam collimator is used as the collimator with the purpose of accurately measuring the attenuation distribution within the object M, truncation correction of the CT image is indispensable.

That is, in a plurality of projection data constituting a single slice of a CT image, projection data collected for individual projection angles within a projection angle range in which the whole portion of the object M is in the effective acquisition field of the detector 22 (hereinafter referred to as "first projection data") and the projection data collected for individual projection angles in the projection angle range in which a part of the portion is outside the effective acquisition field of the detector 22 and truncation is generated (hereinafter referred to as "second projection data").

Figure 2:
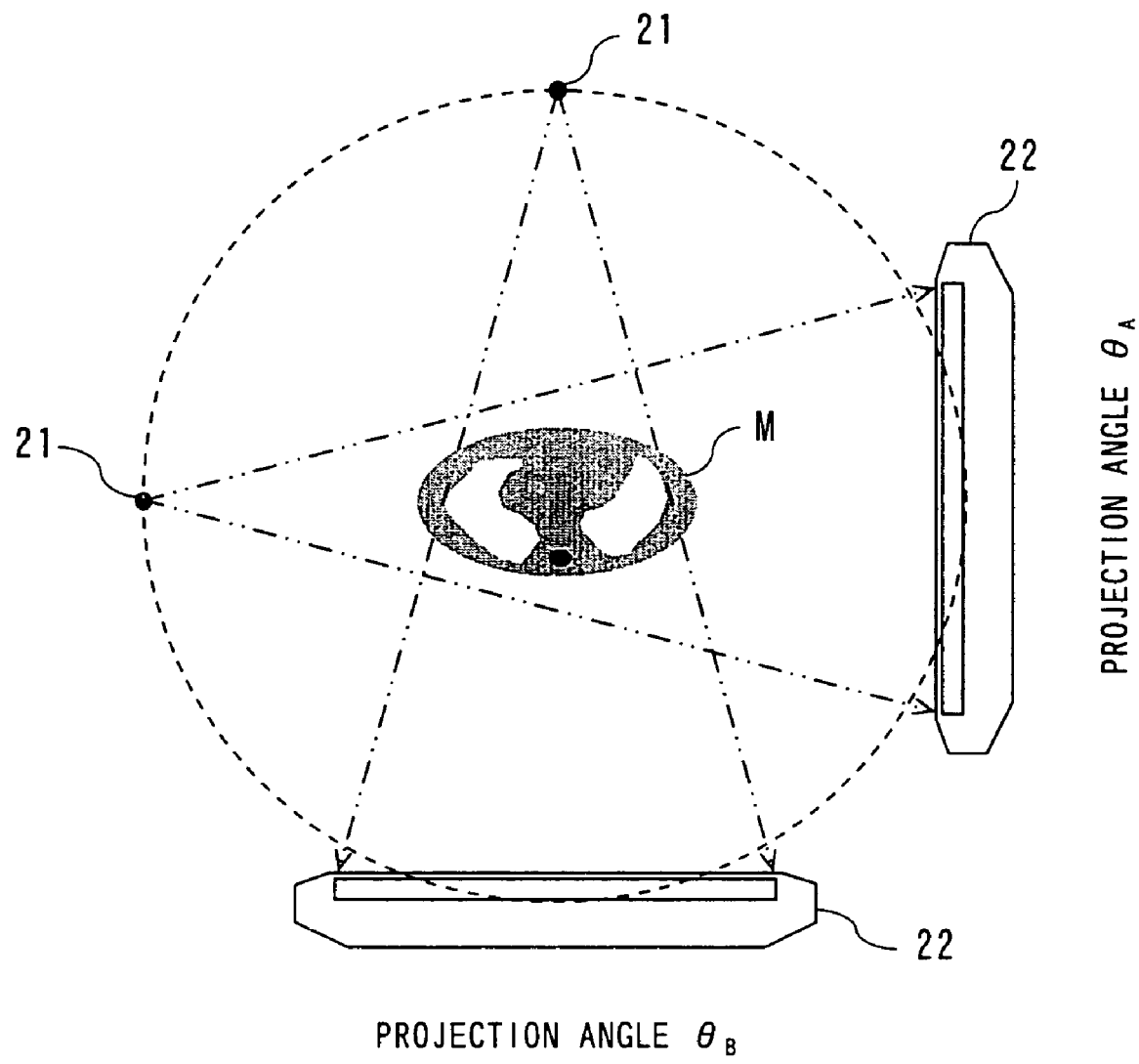
FIG. 2 is a view for explaining an outline of generation of truncation.

FIG. 2 is a view for explaining an outline of generation of truncation.

FIG. 2 shows the gamma radiation source 21 and the detector 22 shown in FIG. 1. At a position of a projection angle in a projection angle range in which the whole portion of the object M is within an effective acquisition field of the detector 22, a projection angle $\theta_A$, for example, the first projection data without generation of truncation is collected. On the other hand, at a position of a projection angle in a projection angle range in which a part of the portion of the object M is outside the effective acquisition field of the detector 22, a projection angle $\theta_B$, for example, the second projection data with generation of truncation is collected.

Figure 3:
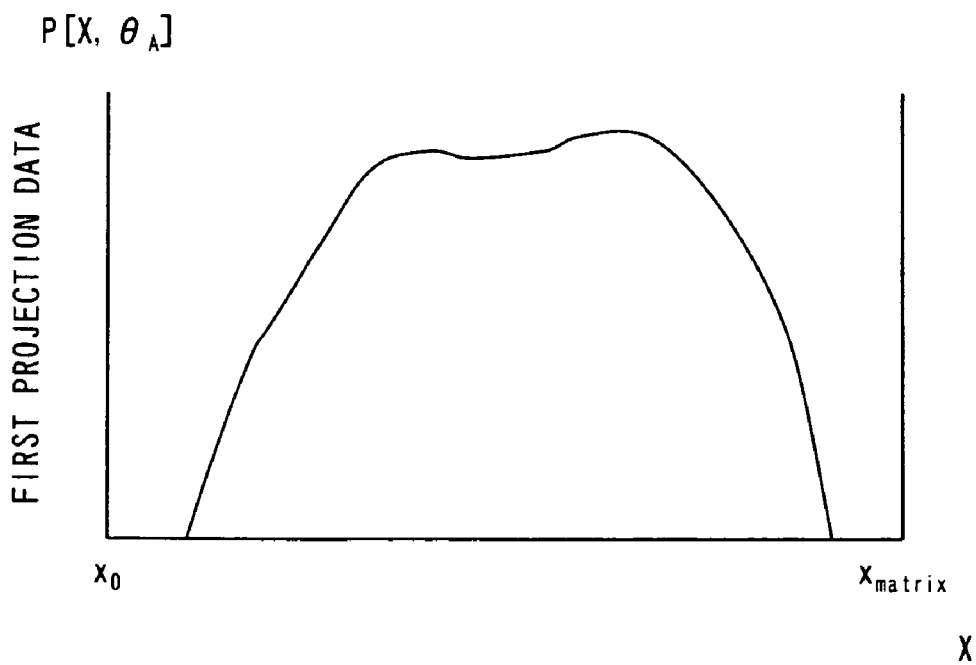
FIG. 3 is an example of a profile curve of a projection data collected by a CT data collection unit.
Figure 4:
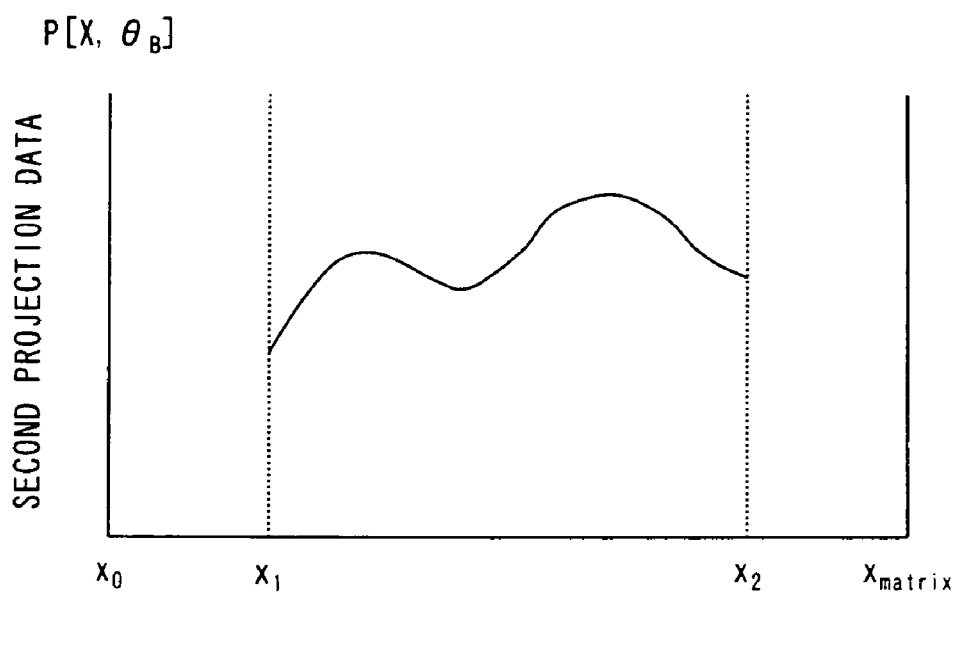
FIG. 4 is an example of a profile curve of a projection data collected by a CT data collection unit.

FIGS. 3 and 4 show examples of a profile curve of the projection data collected by the CT data collection unit 41.

FIG. 3 is a profile curve of the first projection data $P[X, \theta_A]$ in which a count value of the gamma radiation falling on the detector 22 at a position of the projection angle $\theta_A$ shown in FIG. 2 is shown in terms of a measurement position direction X (one end $x_0$ of the detector 22<X<the other end of the detector 22 $x_{matrix}$). On the other hand, FIG. 4 is a profile curve of the second projection data $P[X, \theta_B]$ in which a count value of the gamma radiation falling on the detector 22 at a position of the projection angle $\theta_B$ shown in FIG. 2 is shown in terms of a measurement position direction X. In FIG. 4, the gamma radiation is not counted in the range of $X<x_1$, $x_2<X$, and truncation is generated.

The primary correction unit 42 of the PET-CT apparatus 10A shown in FIG. 1 estimates a truncated portion of the second projection data, sequentially acquires a primary extrapolation expression for correcting (extrapolating) the truncated portion and corrects the second projection data with the primary extrapolation expression. At the primary correction unit 42, a nature of the CT data, that is, when truncation is not generated, "a total sum value of projection data is constant at all the projection angles" and "all the integration values (center of gravity) weighted in the measurement position direction of the CT image are fixed when seen from all the projection angles" is used.

That is, the primary correction unit 42 obtains third projection data formed from the second projection data and the primary extrapolation expression as substitute data for the second projection data when the nature of the CT data is used and there is a projection angle at which a part of the portion protrudes out of the effective acquisition field of the detector 22.

The primary correction unit 42 is provided with a total sum value calculation unit 51, a primary extrapolation expression candidate calculation unit 52, a third projection data candidate acquisition unit 53, a center of gravity calculation unit 54, a fitting processing unit 55 and a third projection data extraction unit 56.

The total sum value calculation unit 51 calculates a total sum value (0th moment) for individual projection data collected by the CT data collection unit 41. That is, the total sum value calculation unit 51 calculates the 0th moment of the first projection data and the 0th moment of the second projection data, respectively.

The primary extrapolation expression candidate calculation unit 52 calculates a plurality of primary extrapolation expression candidates for correcting the truncated portion of the second projection data on the basis of a difference between the 0th moment of the first projection data and the 0th moment of the second projection data calculated by the total sum value calculation unit 51. For example, the primary extrapolation expression candidate calculation unit 52 acquires an average value of the 0th moments of each of the plurality of first projection data and calculates the plurality of primary extrapolation expression candidates on the basis of a difference between the average value and the 0th moment of the second projection data.

The third projection data candidate acquisition unit 53 corrects the second projection data for each of the primary extrapolation expression data candidates and obtains a plurality of third projection data candidates formed from the second projection data and the primary extrapolation expression candidate.

The center of gravity calculation unit 54 calculates a center of gravity (1st moment) of each of the plurality of first projection data collected by the CT data collection unit 41 and the 1st moment of each of the plurality of third projection data candidates obtained by the third projection data candidate acquisition unit 53, respectively.

The fitting processing unit 55 conducts fitting processing of the relation between the 1st moment of each of the first projection data calculated by the center of gravity calculation unit 54 and the projection angle to a trigonometric function (sin curve).

The third projection data extraction unit 56 obtains third projection data from the plurality of third projection data candidates on the basis of a difference between the 1st moment of the third projection data estimated from the 1st moments of the plurality of first projection data and the 1st moment of the plurality of third projection data candidates calculated at the center of gravity calculation unit 54. Specifically, the third projection data extraction unit 56 extracts as the third projection data the third projection data candidate having the 1st moment at which a difference between the 1st moment of the third projection data estimated from the sin curve after processing at the fitting processing unit 55 and the 1st moment of each of the plurality of third projection data candidates calculated at the center of gravity calculation unit 54 becomes the minimum.

The body contour detection unit 43 detects position information of the body contour of the object M in the second projection data by detecting the body contour on the basis of the third projection data extracted by the third projection data extraction unit 56.

The secondary correction unit 44 obtains fourth projection data formed from the second projection data and a secondary extrapolation expression by correcting the second projection data with the secondary extrapolation expression of multi-degree expression in a general method on the basis of the position information of the body contour detected by the body contour detection unit 43.

The reconstruction unit 45 reconstructs the CT image on a slice-by-slice basis on the basis of the first projection data collected by the CT data collection unit 41 and the fourth projection data obtained by the secondary correction unit 44.

Moreover, the PET-CT apparatus 10A is provided with an attenuation distribution correction unit 61 for measuring an attenuation distribution on the basis of the first projection data and the fourth projection data and performing attenuation-correction of PET data obtained by the PET apparatus 11 with this measured amount, and an output unit 62 for outputting the CT image reconstructed by the reconstruction unit 45 and the PET data outputted from the attenuation distribution correction unit 61 to the outside.

It is to be noted that each of the units provided in the PET-CT apparatus 10A may be configured as hardware or they may function by a program executed by CPU (not shown).

Next, operation of the PET-CT apparatus 10A as the radio-diagnostic apparatus 10 will be described.

The PET apparatus 11 of the PET-CT apparatus 10A shown in FIG. 1 detects the gamma radiation emitted from RI dosed to the object M and collects PET data.

On the other hand, the transmission CT apparatus 12 radiates the gamma radiation from the gamma radiation source 21 to the object M, and the gamma radiation having transmitted through the object M falls on the detector 22 from the collimator 23. The CT data collection unit 41 receives electric signals for 360 degrees at a plurality of projection angles while rotating the gamma radiation source 21 and the detector 22 around the axis of the object M and collects them as the projection data for individual projection angles.

The primary correction unit 42 obtains the second projection data that a part of the portion of the object M becomes out of the effective acquisition field of the detector 22 and truncation is generated from the projection data collected at individual projection angles and estimates the truncated portion. Then, the primary correction unit 42 corrects the truncated portion of the second projection data by the primary extrapolation expression and obtains the third projection data formed from the second projection data and the primary extrapolation expression.

Specifically, first, the total sum value calculation unit 51 provided at the primary correction unit 42 calculates the 0th moment of the first projection data taken for each of all the measurement position directions for individual projection angles in the projection angle range in which the whole portion of the object M is within the effective acquisition field of the detector 22 and truncation is not generated. Similarly, the 0th moment of the second projection data is calculated for individual projection angles in the projection angle range in which the truncation is generated. The primary correction unit 42 calculates the 0th moment $M_0 [\theta_A]$ of the projection data $P[X, \theta_A]$ collected at a projection angle in the projection angle range in which the truncation is not generated, at the projection angle $\theta_A$ shown in FIG. 2, for example, and the 0th moment $I_0 [\theta_B]$ of the projection data $P[X, \theta_B]$ collected at the projection angle $\theta_B$ shown in FIG. 2, for example, by the following expression, respectively:

$$M_0 [\theta_A] = \Sigma P[X, \theta_A] \quad (x_0 < X < x_{matrix}) \qquad \text{Expression (1)}$$

$$I_0 [\theta_B] = \Sigma P[X, \theta_B] \quad (x_0 < X < x_{matrix}) \qquad \text{Expression (2)}$$

Figure 5:
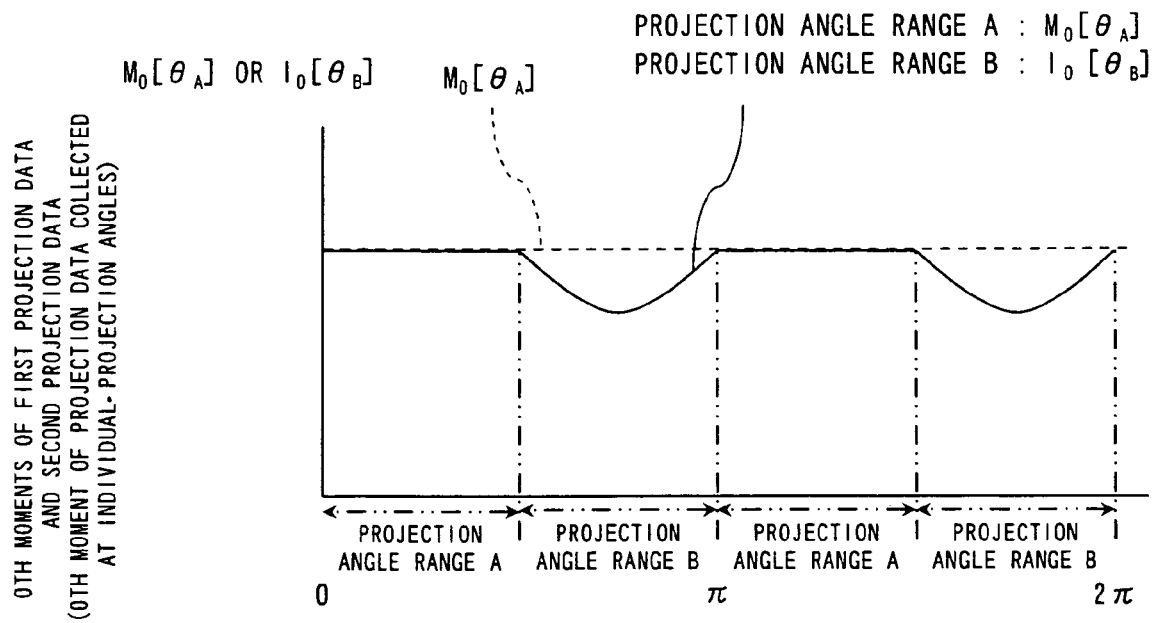
FIG. 5 is a graph of an example of a relation between a projection angle and a 0th moment of a projection data collected at individual projection angles

FIG. 5 shows a graph of an example of the relation between the projection angle and the 0th moment of the projection data collected at individual projection angles.

From the nature of the projection data, in the relation between a projection angle θ and the 0th moment of the projection data corresponding to the projection angle θ in an ideal case that truncation is not generated in the projection data at all the projection angles θ, the 0th moment becomes a constant value ($M_0 [\theta_A]$) irrespective of the projection angle θ. However, in the relation between the projection angle θ and the 0th moment in the case where the truncation is generated in the projection data, the 0th moment of the second projection data collected at a projection angle in a projection angle range B becomes smaller than the 0th moment of the first projection data collected at a projection angle in a projection angle range A at which the truncation is not generated. Moreover, a waveform of the 0th moment of the second projection data collected at the projection angle in the projection angle range B draws a curve of a substantially trigonometric function with change of the projection angle in the projection angle range B. That is because, in the case of the projection angle in the projection angle range B, data is not obtained in the range of $X < X_1$, $x_2 < X$ shown in FIG. 4, and the 0th moment becomes smaller than those at the projection angle in the projection angle range A.

The primary extrapolation expression candidate calculation unit 52 of the primary correction unit 42 shown in FIG. 1 averages a plurality of the 0th moments $M_0 [\theta_A]$ calculated by the expression (1). The primary extrapolation expression candidate calculation unit 52 compares the 0th moment average value $M_0$ obtained by averaging the 0th moments $M_0 [\theta_A]$ and the 0th moment $I_0 [\theta_B]$ calculated by the expression (2). Specifically, a plurality of primary extrapolation expression candidates satisfying a condition that a difference between the 0th moment average value $M_0$ and the 0th moment $I_0 [\theta_B]$ becomes the minimum is calculated.

Figure 6:
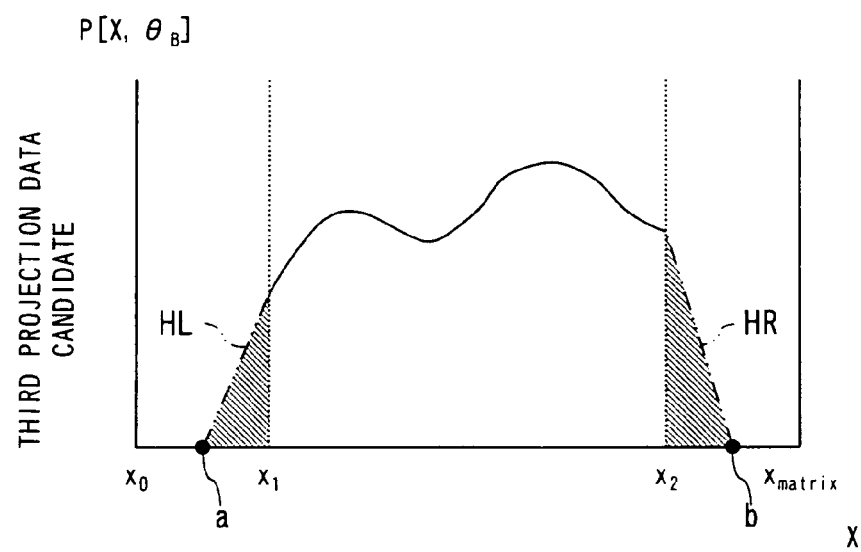
FIG. 6 is a diagram explaining a method for calculating the plurality of primary extrapolation expression candidates.

FIG. 6 is a diagram explaining a method for calculating the plurality of primary extrapolation expression candidates.

FIG. 6 shows the second projection data $P[X, \theta_B]$ shown in FIG. 4, a moving point a moving on the X-axis within a range of $x_0 < a < x_1$ and a moving point b moving within a range of $x_2 < b < x_{matrix}$. Here, a difference between the 0th moment average value $M_0$, an average value of the 0th moments collected per projection angle $\theta_A$ at which the truncation is not generated and the 0th moment $I_0 [\theta_B]$ of the second projection data $P[X, \theta_B]$ calculated by the expression (2) equals an area formed by the primary extrapolation expression and the X-axis. For example, supposing that the primary extrapolation expression is a linear expression, since the difference between the 0th moment average value $M_0$ and the 0th moment $I_0 [\theta_B]$ equals an area shown by a shaded unit in FIG., the following equation is true:

$$M_0 - I_0[\theta_B] = \frac{P[x_1, \theta_B] \times (x_1 - a)}{2} + \frac{P[x_2, \theta_B] \times (b - x_2)}{2} \quad \text{Expression (3)}$$

From this expression (3), the relation between the moving point a and the moving point b is determined and a plurality of primary extrapolation expression candidates H, that is, a plurality of candidates of the body contour (between a and b) is calculated from the moving point a moving in the range of $x_0 < a < x_1$ and the point b determined by the position of the moving point a. The primary extrapolation expression candidates H consist of a primary extrapolation expression candidate HL passing through a scan rotating-coordinate system (a, 0) and $(x_1, P[X_1, \theta_B])$ in the range of $a \leq X \leq x_1$ and a primary extrapolation expression candidate HR passing through the scan rotating coordinate system $(x_2, P[X_2, \theta_B])$ and (b, 0) in the range of $x_2 \leq X \leq b$.

Here, explanation will be made for the case where the primary extrapolation expression is a linear expression, but the primary extrapolation expression is not limited to the linear expression but it may be a trigonometric function or a multi-degree expression.

The third projection data candidate acquisition unit 53 shown in FIG. 1 corrects the truncated portion of the second projection data with the plurality of primary extrapolation expression candidates. And the plurality of third projection data candidates formed from the second projection data P [X, $\theta_B$] in the range of $x_1 < X < x_2$ shown in FIG. 6 and the plurality of primary extrapolation expression candidates H in the ranges of $a \leq X \leq x_1$ and $x_2 \leq X \leq b$ is obtained.

The center of gravity calculation unit 54 calculates the 1st moment per the third projection data candidate. Also, the center of gravity calculation unit 54 calculates the 1st moment of the first projection data per projection angle in the projection angle range in which the truncation is not generated.

The fitting processing unit 55 conducts fitting processing of the 1st moment calculated for individual projection angles in the projection angle range in which the truncation is not generated to a sin curve at the center of gravity calculation unit 54.

The third projection data extraction unit 56 extracts as the third projection data the third projection data candidate having the 1st moment at which a difference between the 1st moment of the third projection data estimated from the sin curve after processing at the fitting processing unit 55 and the 1st moment of each of the plurality of third projection data candidates calculated by the center of gravity calculation unit 54 becomes the minimum.

Figure 7:
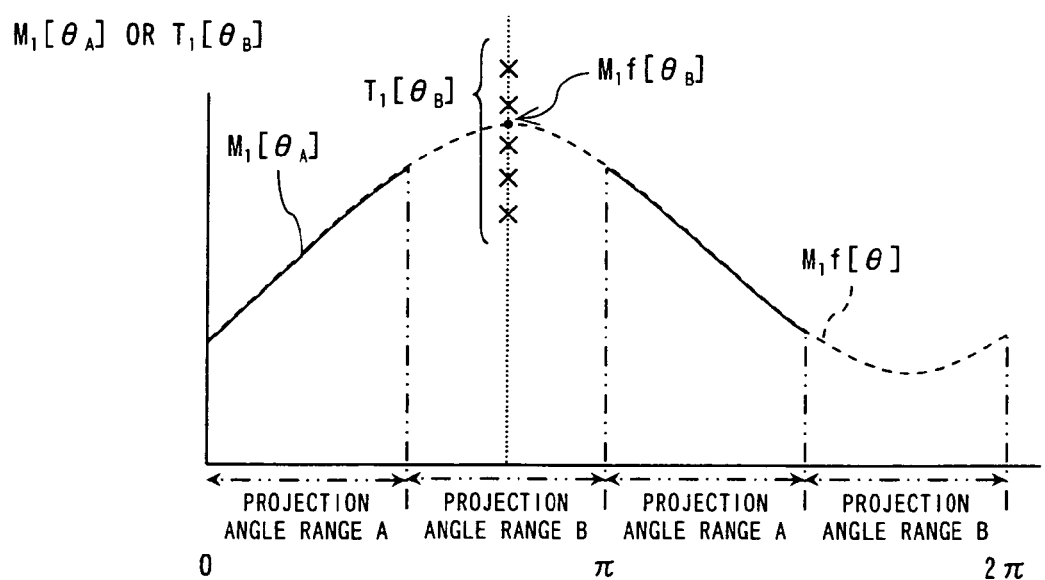
FIG. 7 is a graph of an example of a relation between a projection angle in a projection angle range in which a truncation is not generated and a 1st moment of a projection data collected per projection angle.

FIG. 7 shows a graph of an example of the relation between the projection angle in the projection angle range in which the truncation is not generated and the 1st moment of the projection data collected per projection angle.

From the nature that all the integration values weighted in the measurement position direction of the CT image are fixed when seen from all the projection angles, the 1st moment $M_1[\theta_A]$ calculated at the center of gravity calculation unit 54 per projection angle $\theta_A$ in the projection angle range in which the truncation is not generated is fitting-processed to the sin curve $M_1 f[\theta]$.

Then, the 1st moment $T_1[\theta_B]$ at which a difference between the 1st moment $T_1[\theta_B]$ (cross marks in FIG. 7) of each of the plurality of third projection data candidates calculated by the center of gravity calculation unit 54 and the point $M_1 f[\theta_B]$ on the sin curve $M_1 f[\theta]$ obtained at the fitting processing unit 55 becomes the minimum is identified. And the third projection data candidate having the 1st moment $T_1[\theta_B]$ at which the difference becomes the minimum is extracted as the third projection data.

As mentioned above, according to the primary correction unit 42 shown in FIG. 1, the third projection data formed from the second projection data and the primary extrapolation expression can be obtained by correcting the truncated portion of the second projection data with an appropriate primary expression per projection angle in the projection angle range in which the truncation is generated.

Then, the body contour detection unit 43 detects the position information of the body contour in the second projection data by detecting the body contour on the basis of the third projection data extracted at the third projection data extraction unit 56. Thus, the body contour detection unit 43 can detect the position information of the body contour on the projection data of all the projection angles required for reconstruction of the CT image by detecting the position information of the body contour of the second projection data at all the projection angles on a slice-by-slice basis in the projection angle range in which the truncation is generated. Also, the body contour detection unit 43 may detect the position information of the body contour in the second projection data by binary-coding the third projection data obtained by the primary correction unit 42 through setting of a threshold value on a slice-by-slice basis and back projection of this binary-coded data. It is preferable that this body contour is given fitting processing for smoothening by 7th-degree Fourier transformation. It is to be noted that the degree in this fitting processing is not limited to the 7th.

The secondary correction unit 44 obtains the fourth projection data formed from the second projection data and the secondary extrapolation expression by correcting the second projection data with the secondary extrapolation expression of multi-degree expression in a general method using the data representing the body contour detected by the body contour detection unit 43.

The reconstruction unit 45 reconstructs the CT image on a slice-by-slice basis on the basis of the first projection data collected by the CT data collection unit 41 and the fourth projection data obtained by the secondary correction unit 44.

The attenuation distribution correction unit 61 measures the attenuation distribution on the basis of the first projection data collected by the CT data collection unit 41 and the fourth projection data obtained by the secondary correction unit 44 and attenuation-corrects the PET data collected by the PET apparatus 11 by this measurement amount.

The output unit 62 outputs the CT image reconstructed at the reconstruction unit 45 and the PET data outputted from the attenuation distribution correction unit 61 to the outside.

Figure 8:
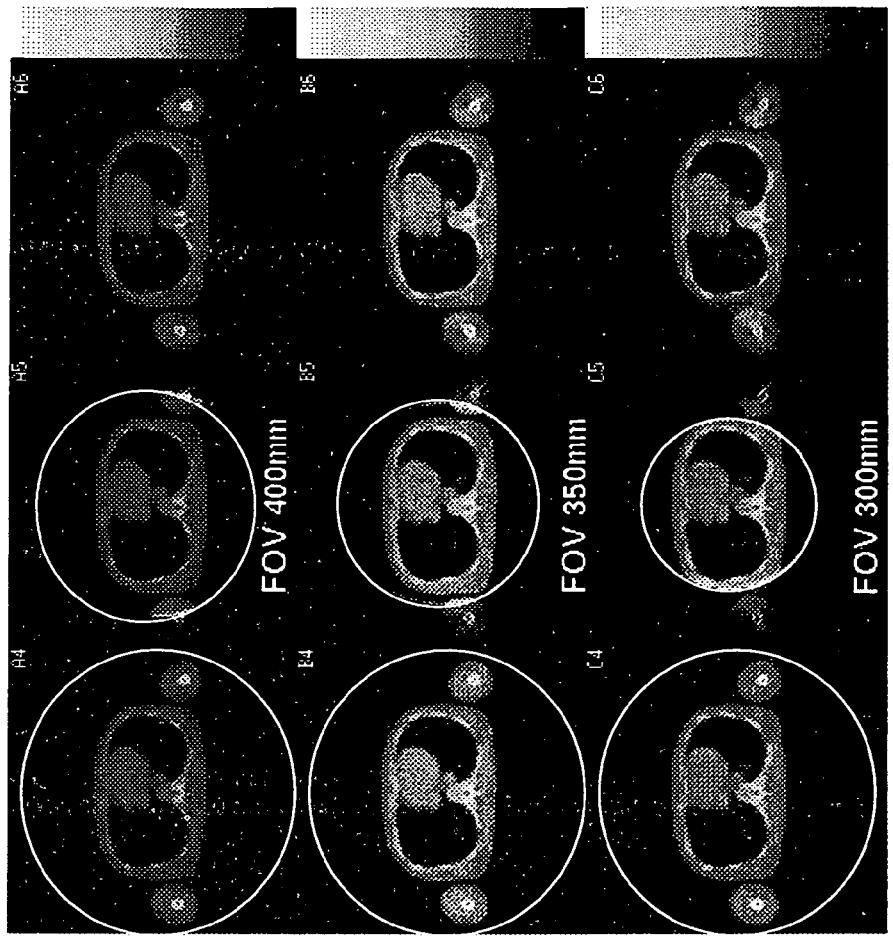
FIG. 8 is a view showing CT images outputted from an output unit to a screen.

FIG. 8 is a view showing the CT images outputted from the output unit 62 to a screen.

On the screen shown in FIG. 8, 3×3 CT images of a breast part actually measured on the object M with the arms down are displayed. An upper row on the screen shows the case where the collimator 23 has a virtual acquisition field size of 400 mm, a middle row for the case where the collimator 23 has a virtual acquisition field size of 350 mm and an lower row for the case where the collimator 23 has a virtual acquisition field size of 300 mm, respectively. Also, a left column on the screen shows the case where truncation is not generated for all the projection data, a middle column for the case where the truncation is generated in a part of the projection data and the secondary correction is made on the basis of the body contour detected by a conventional method from the CT data obtained by the emission CT apparatus, and a right column for the case where the truncation is generated in a part of the projection data and the secondary correction is made on the basis of the body contour detected by the present invention from the CT data obtained by the emission CT apparatus.

According to the screen shown in FIG. 8, the shape of the truncated portion can be recovered for the cases with the virtual acquisition field sizes of 400, 350 and 300 mm, and particularly the shape of the truncated portion is favorably recovered with the case of the virtual acquisition field size of 400 mm. Also, when the virtual acquisition field size is 300 mm, an error of nearly 20% by the truncation can be reduced to about 3%.

As an example of the radiodiagnostic apparatus 10 shown in FIG. 1, the case where the PET-CT apparatus 10A is a complex machine of the emission CT apparatus 11 and the transmission CT apparatus 12 has been described. However, the radiodiagnostic apparatus 10 might be comprised only by the transmission CT apparatus 12, and in that case, the CT image reconstructed at the reconstruction unit 45 is sent to the output unit 62, and the output unit 62 outputs the CT image to the outside.

According to the PET-CT apparatus 10A as the radiodiagnostic apparatus 10 shown in FIG. 1, an attenuation distribution can be accurately measured, and the truncation correction can be made accurately with high accuracy.

Also, according to the PET-CT apparatus 10A as the radiodiagnostic apparatus 10, the body contour with high accuracy can be detected only from the transmission CT apparatus.

What is claimed is:

1. A radiodiagnostic apparatus comprising:
    a data collection unit configured to collect a first projection data obtained at a projection angle within a projection angle range in which the whole portion of an object is within an effective acquisition field of a detector, and configured to collect a second projection data obtained at a projection angle within a projection angle range in which a part of a truncated portion is out of the effective acquisition field of the detector, when the effective acquisition field of the detector is defined as a range limited by a collimator;
    a primary correction unit configured to calculate a plurality of primary extrapolation expression candidates for correcting said second projection data on the basis of a difference between a total sum value of said first projection data and a total sum value of said second projection data so as to obtain a plurality of third projection data candidates formed from said second projection data and said plurality of primary extrapolation expression candidates and configured to obtain third projection data from said plurality of third projection data candidates on the basis of a difference between a center of gravity of the third projection data estimated from the center of gravity of said first projection data and a center of gravity of said plurality of third projection data candidates;
    a body contour detection unit configured to detect position information of a body contour in said second projection data on the basis of said third projection data;
    a secondary correction unit configured to acquire a secondary extrapolation expression for correcting said second projection data on the basis of said position information of the body contour and configured to obtain fourth projection data formed from said second projection data and said secondary extrapolation expression; and
    a reconstruction unit configured to reconstruct an image on a slice-by-slice basis on the basis of said first projection data and said fourth projection data.

2. The radiodiagnostic apparatus according to claim 1, wherein said primary extrapolation expression is a linear expression.

3. The radiodiagnostic apparatus according to claim 1, wherein said primary extrapolation expression is a trigonometric function or a multi-degree expression.

4. The radiodiagnostic apparatus according to claim 1, wherein, when said collimator is a fan beam collimator, said data collection unit conducts processing to convert fan beam data collected as said first projection data and said second projection data to parallel beam data.

5. The radiodiagnostic apparatus according to claim 1, wherein said primary correction unit further comprises a total sum value calculation unit configured to individually calculate total sum values of said first projection data and said second projection data, a primary extrapolation expression candidate calculation unit configured to calculate said plurality of primary extrapolation expression candidates so that the total sum value of said first projection data equals the total sum value of said third projection data, a third projection data candidate acquisition unit configured to acquire said plurality of third projection data candidates, a center of gravity calculation unit configured to individually calculate a center of gravity of each of said plurality of first projection data and a center of gravity of each of said plurality of third projection data, a fitting processing unit configured to conduct fitting processing of the center of gravity of each of said plurality of first projection data to a trigonometric function, and a third projection data extraction unit configured to extract as said third projection data said third projection data candidate having the center of gravity at which a difference between the center of gravity of each of said plurality of third projection data and said trigonometric function becomes the minimum.

6. The radiodiagnostic apparatus according to claim 1, further comprising an output unit configured to output an image reconstructed by said reconstruction unit or an output from said attenuation distribution correction unit to the outside.

7. A radiodiagnostic apparatus comprising:
    a data collection unit configured to collect a first projection data obtained at a projection angle within a projection angle range in which the whole portion of an object is within an effective acquisition field of a detector, and configured to collect a second projection data obtained at a projection angle within a projection angle range in which a part of a truncated portion is out of the effective acquisition field of the detector, when the effective acquisition field of the detector is defined as a range limited by a collimator;
    a primary correction unit configured to calculate a plurality of primary extrapolation expression candidates for correcting said second projection data on the basis of a difference between a total sum value of said first projection data and a total sum value of said second projection data so as to obtain a plurality of third projection data candidates formed from said second projection data and said plurality of primary extrapolation expression candidates and configured to obtain third projection data from said plurality of third projection data candidates on the basis of a difference between a center of gravity of the third projection data estimated from said first projection data and a center of gravity of said plurality of third projection data candidates;
    a body contour detection unit configured to detect position information of a body contour in said second projection data on the basis of said third projection data;

a secondary correction unit configured to acquire a secondary extrapolation expression for correcting said second projection data on the basis of said position information of the body contour and configured to obtain fourth projection data formed from said second projection data and said secondary extrapolation expression; and an attenuation distribution correction unit configured to measure an attenuation distribution on the basis of said first projection data and said fourth projection data and configured to correct emission data on the basis of said attenuation distribution.

8. The radiodiagnostic apparatus according to claim 7, wherein said primary extrapolation expression is a linear expression.

9. The radiodiagnostic apparatus according to claim 7, wherein said primary extrapolation expression is a trigonometric function or a multi-degree expression.

10. The radiodiagnostic apparatus according to claim 7, wherein, when said collimator is a fan beam collimator, said data collection unit conducts processing to convert fan beam data collected as said first projection data and said second projection data to parallel beam data.

11. The radiodiagnostic apparatus according to claim 7, wherein said primary correction unit further comprises a total sum value calculation unit configured to individually calculate total sum values of said first projection data and said second projection data, a primary extrapolation expression candidate calculation unit configured to calculate said plurality of primary extrapolation expression candidates so that the total sum value of said first projection data equals the total sum value of said third projection data, a third projection data candidate acquisition unit configured to acquire said plurality of third projection data candidates, a center of gravity calculation unit configured to individually calculate a center of gravity of each of said plurality of first projection data and a center of gravity of each of said plurality of third projection data, a fitting processing unit configured to conduct fitting processing of the center of gravity of each of said plurality of first projection data to a trigonometric function, and a third projection data extraction unit configured to extract as said third projection data said third projection data candidate having the center of gravity at which a difference between the center of gravity of each of said plurality of third projection data and said trigonometric function becomes the minimum.

12. The radiodiagnostic apparatus according to claim 7, further comprising a reconstruction unit configured to reconstruct an image on a slice-by-slice basis on the basis of said first projection data and said fourth projection data.

13. The radiodiagnostic apparatus according to claim 12, further comprising an output unit configured to output an image reconstructed by said reconstruction unit to the outside.

14. The radiodiagnostic apparatus according to claim 7, further comprising an output unit configured to output an output from said attenuation distribution correction unit to the outside.

* * * * *

UNITED STATES PATENT AND TRADEMARK OFFICE
CERTIFICATE OF CORRECTION

PATENT NO. : 7,502,440 B2 Page 1 of 1
APPLICATION NO. : 11/396450
DATED : March 10, 2009
INVENTOR(S) : Motomura et al.

It is certified that error appears in the above-identified patent and that said Letters Patent is hereby corrected as shown below:

On the title page, Item (73), the Assignees' information is incorrect. Item (73) should read:

Item -- (73) Assignee: Kabushiki Kaisha Toshiba, Tokyo (JP); Toshiba Medical Systems Corporation, Otawara-Shi (JP) --

Signed and Sealed this

Twenty-sixth Day of May, 2009

JOHN DOLL
*Acting Director of the United States Patent and Trademark Office*